(12) United States Patent
Ono et al.

(10) Patent No.: US 9,463,359 B2
(45) Date of Patent: Oct. 11, 2016

(54) REHABILITATION ASSISTANCE SYSTEM

(71) Applicant: NIHON KOHDEN CORPORATION, Tokyo (JP)

(72) Inventors: Yoshinobu Ono, Tokyo (JP); Hiroyuki Matsumoto, Tokyo (JP); Masahiro Yade, Tokyo (JP); Yuka Minegishi, Tokyo (JP); Takehito Suzuki, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 0 days.

(21) Appl. No.: 14/677,473

(22) Filed: Apr. 2, 2015

(65) Prior Publication Data

US 2015/0297950 A1 Oct. 22, 2015

(30) Foreign Application Priority Data

Apr. 16, 2014 (JP) ................. 2014-084725

(51) Int. Cl.
*A63B 24/00* (2006.01)
*A63B 23/16* (2006.01)
(Continued)

(52) U.S. Cl.
CPC ............ *A63B 24/0062* (2013.01); *A61B 5/11* (2013.01); *A61B 5/1124* (2013.01); *A61B 5/1125* (2013.01); *A61B 5/4082* (2013.01); *A61B 5/6826* (2013.01); *A63B 21/1453* (2013.01); *A63B 23/16* (2013.01); *A63F 3/00574* (2013.01); *A63F 3/00643* (2013.01);
(Continued)

(58) Field of Classification Search
CPC ............ G09B 1/02; G09B 1/06; G09B 1/04; G09B 1/10; G09B 5/06; A63B 24/00; A63B 24/0062; A63B 23/16; A63B 2220/44; A63B 2220/58; A63B 2220/74; A63B 2220/803; A63B 2024/0068; A63B 21/1453
See application file for complete search history.

(56) References Cited

U.S. PATENT DOCUMENTS 4,176,470 A * 12/1979 Fosner ............... G09B 1/10
434/259
5,372,511 A * 12/1994 Keung ............... G09B 5/06
434/327

(Continued)

FOREIGN PATENT DOCUMENTS

EP 1 594 039 A1 11/2005
JP 2010-284293 A 12/2010
(Continued)

OTHER PUBLICATIONS

Giuseppe Placidi, "A smart virtual glove for the hand telerehabilitation"; Computers in Biology and Medicine; New York, US; vol. 37, No. 8, Jul. 26, 2007; pp. 1100-1107; XP022170973.
(Continued)

Primary Examiner — Glenn Richman
(74) Attorney, Agent, or Firm — Pearne & Gordon LLP

(57) ABSTRACT

A rehabilitation assistance system includes a peg board, a peg to be placed on the peg board by a subject, and a position information acquisition unit that acquires position information indicating a position of the peg relative to a predetermined position on the peg board. The position information acquisition unit includes a sensor provided on at least one of the peg and the peg board, and the position information acquisition unit acquires the position information based on an output from the sensor.

15 Claims, 9 Drawing Sheets

(51) Int. Cl.
*A63B 21/00* (2006.01)
*A63F 3/00* (2006.01)
*A61B 5/11* (2006.01)
*A61B 5/00* (2006.01)
*A63F 9/00* (2006.01)
*G06F 3/041* (2006.01)

(52) U.S. Cl.
CPC .......... *A61B5/1123* (2013.01); *A61B 2505/09* (2013.01); *A63B 2024/0068* (2013.01); *A63B 2220/44* (2013.01); *A63B 2220/58* (2013.01); *A63B 2220/74* (2013.01); *A63B 2220/803* (2013.01); *A63F 2003/00662* (2013.01); *A63F 2009/0007* (2013.01); *G06F 3/041* (2013.01)

(56) References Cited

U.S. PATENT DOCUMENTS

| | | | | |
|---|---|---|---|---|
| 5,813,861 | A * | 9/1998 | Wood | G09B 1/04 434/167 |
| 5,882,011 | A * | 3/1999 | Praria | A63F 9/0096 273/237 |
| 6,371,931 | B1 | 4/2002 | Guillen | |
| 6,659,836 | B1 * | 12/2003 | Yamasaki | G09B 1/06 273/237 |
| 7,214,066 | B2 * | 5/2007 | Marcus | G09B 1/06 434/156 |
| 7,295,124 | B2 * | 11/2007 | Guillen | A61B 5/162 340/539.12 |
| 8,435,037 | B1 * | 5/2013 | Davis | G09B 1/02 273/156 |
| 2005/0232467 | A1 | 10/2005 | Mohri et al. | |
| 2007/0265146 | A1 | 11/2007 | Kowalczewski et al. | |
| 2012/0302925 | A1 | 11/2012 | Craelius et al. | |

FOREIGN PATENT DOCUMENTS

| | | |
|---|---|---|
| JP | 2012-231817 A | 11/2012 |
| WO | 2007/131340 A1 | 11/2007 |

OTHER PUBLICATIONS

Michela Borghetti et al., "Sensorized Glove for Measuring Hand Finger Flexion for Rehabilitation Purposes"; IEEE Transactions on Instrumentation and Measurement; IEEE Service Center, Piscataway, NJ, US; vol. 62, No. 12, Dec. 1, 2013; pp. 3308-3314; XP011531505.

Extended European Search Report for the related European Patent Application No. 15163091.0 dated Oct. 27, 2015.

* cited by examiner

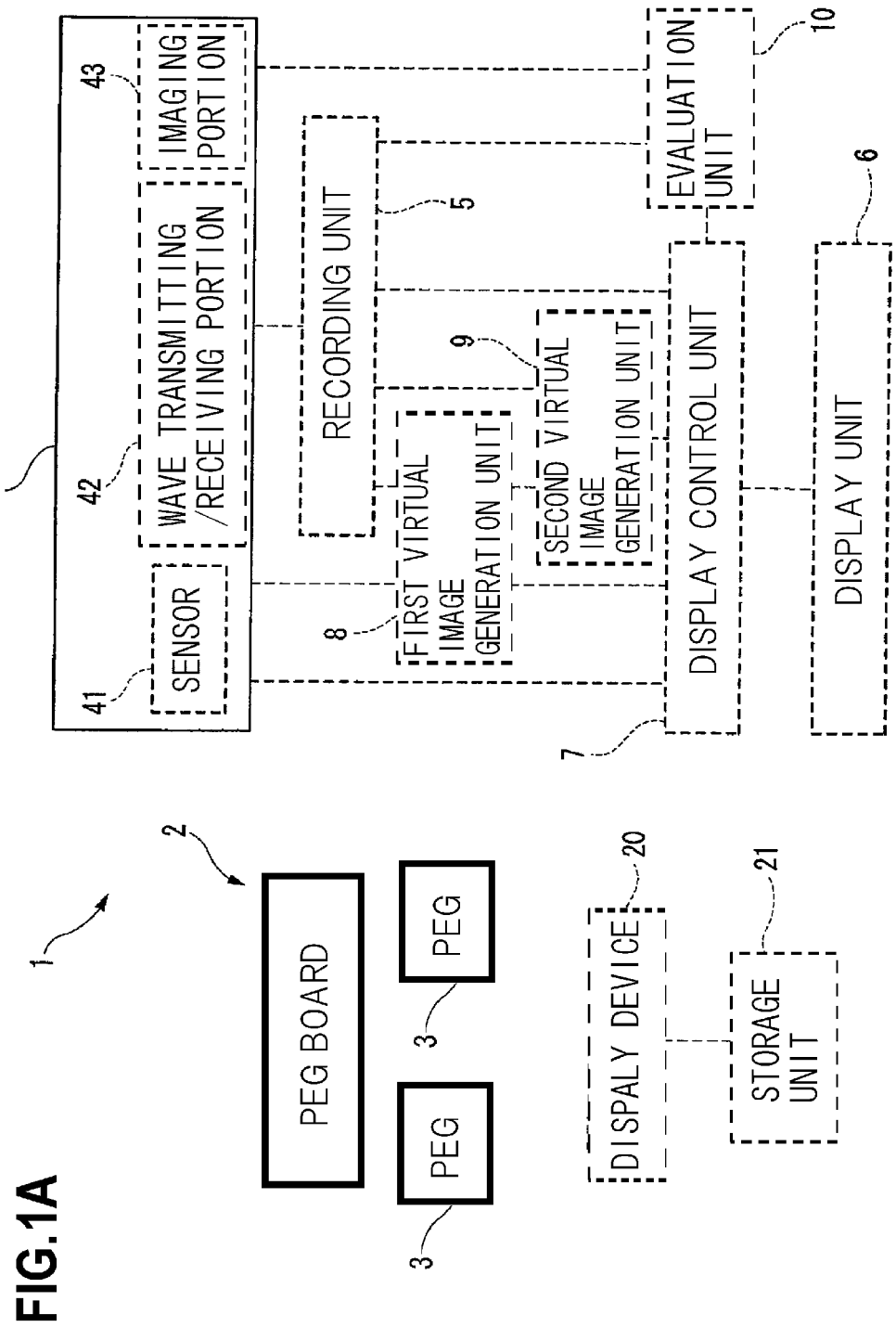

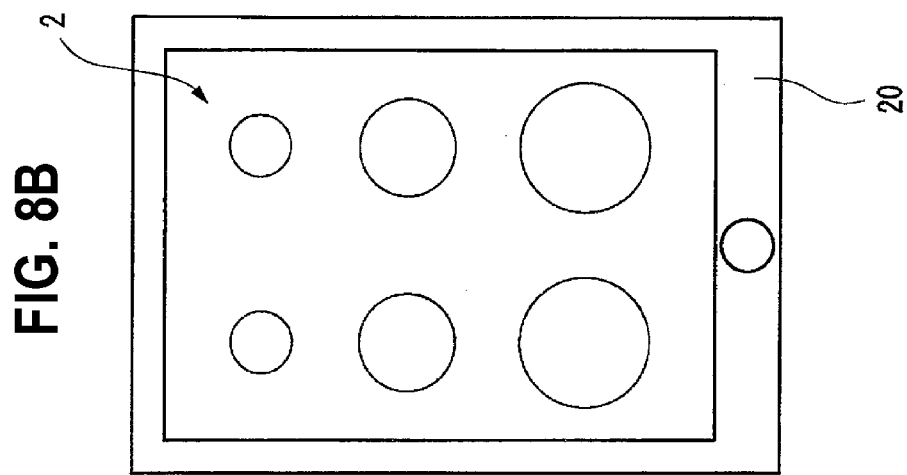
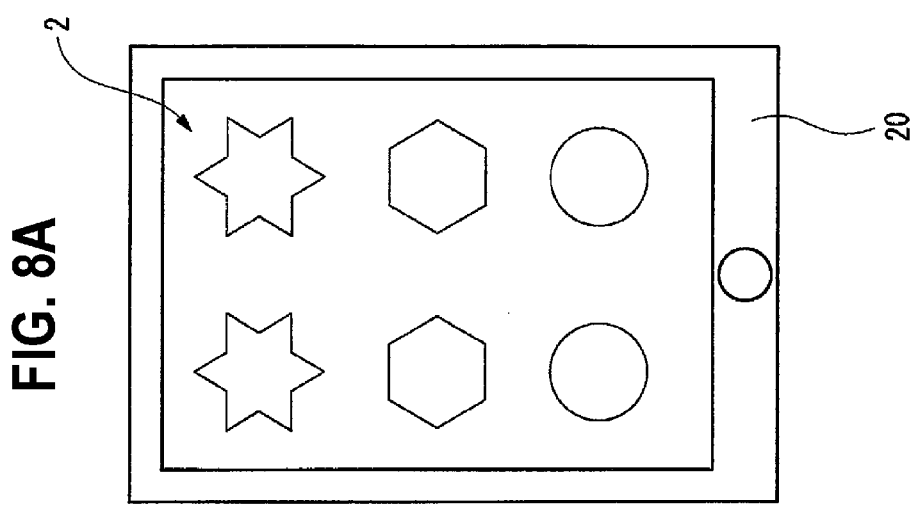

REHABILITATION ASSISTANCE SYSTEM

CROSS REFERENCE TO RELATED APPLICATION

This application is based on Japanese Patent Applications No. 2014-084725 filed on Apr. 16, 2014, the contents of which are incorporated herein by reference.

BACKGROUND

The present invention relates to a system for assisting rehabilitation performed to restore a finger function of a subject.

For such rehabilitation, pegs and a peg board are used. The pegs are rod-shaped members having predetermined shapes and colors. The peg board has holes formed to correspond to shapes and colors of the pegs. A subject inserts a peg into a specified hole of on the peg board while griping the peg by the hand or fingers.

A system for quantitatively evaluating results of rehabilitation using the pegs and the peg board in such a manner is known (e.g., see JP-A-2010-284293).

However, evaluation in the system described in JP-A-2010-284293 is just one based on whether or not the peg is inserted into the hole of the peg board. Therefore, it is needed to quantitatively and objectively perform a more detailed evaluation to accurately evaluate a degree of restoration of the function of the subject.

Accordingly, an object of the present invention is to accurately and objectively evaluate a degree of restoration of a finger function of a subject in more detail.

SUMMARY (1) According to an aspect of the invention, a rehabilitation assistance system includes a peg board, a peg to be placed on the peg board by a subject, and a position information acquisition unit that acquires position information indicating a position of the peg relative to a predetermined position on the peg board.

According to the configuration (1), various information as well as whether or not the peg is inserted into a specified hold of the peg board may be acquired. For example, when the subject cannot place the peg at a moving destination, a conventional configuration can grasp only the fact that the subject does not place the peg at the destination. However, how degree the subject can approach the peg to the specified moving destination may be grasped by referring the position information. In addition, which path the subject moves the peg, how high speed the subject moves the peg, how long time the subject spends moving the peg and the like may be grasped.

(2) In the rehabilitation assistance system of (1), the position information acquisition unit includes a sensor provided on at least one of the peg and the peg board, and the position information acquisition unit acquires the position information based on an output from the sensor.

(3) In the rehabilitation assistance system of (2), the sensor includes at least one of an acceleration sensor, an angular velocity sensor, a magnetic sensor, an atmospheric pressure sensor and a motion sensor.

According to the configurations (2) and (3), a suitable sensor may be selected depending on information desired to be grasped, so that a positional relationship between the peg board and the peg may be accurately grasped.

(4) In the rehabilitation assistance system of (1), the position information acquisition unit includes a wave transmitting portion that outputs a wave having a predetermined wavelength toward the peg board and the peg, and a wave receiving portion that detects the wave outputted from the wave transmitting portion and then reflected by the peg board and the peg, and the position information acquisition unit acquires the position information based on an output from the wave receiving portion.

According to the configuration (4), the positional relationship between the peg board and the peg may be grasped without adding a mechanism, such as a sensor, to conventional peg board and pegs.

(5) In the rehabilitation assistance system of (1), the position information acquisition unit includes a imaging portion for picturing the peg board and the peg, and the position information acquisition unit acquires the position information based on an image obtained by the imaging portion.

According to the configuration (5), the positional relationship between the peg board and the peg may be grasped without adding a mechanism, such as a sensor, to conventional peg board and pegs.

(6) In the rehabilitation assistance system of (5), the position information acquisition unit acquires the position information of the peg by extracting a feature point in the image obtained by the imaging portion.

According to the configuration (6), an accuracy of image recognition may be more enhanced.

(7) The rehabilitation assistance system of any one of (1) to (6) further includes a recording unit that records the position information in association with at least acquisition date and time of the position information.

In the configuration (7), at least the past training information and the current training information may be compared in terms of position information, speed and time as well as whether or not the peg is inserted into a hole at a specified moving destination.

(8) The rehabilitation assistance system of any one of (1) to (7) further includes a display unit that is visible by the subject, and a display control unit that displays on the display unit at least one of the position information and an image based on the position information.

According to the configuration (8), the subject may also visually identify results of training or progressions and effects of rehabilitation.

(9) The rehabilitation assistance system of (8) further includes a first virtual image generation unit that generates a virtual image based on the position information as the image to be displayed on the display unit.

(10) The rehabilitation assistance system of (8) or (9) further includes a second virtual image generation unit that generates a virtual image based on information related to an achievement target for rehabilitation as the image to be displayed on the display unit.

According to the configurations (9) and (10), results of training or progressions and effects of rehabilitation may be visually identified even in the case of a configuration in which the imaging portion is not included. Also, because the virtual image may be generated if position information is stored, a data storage capacity therefor may be limited relative to that for image data.

(11) The rehabilitation assistance system of any one of (8) to (10) further includes an evaluation unit that evaluates at least one of progression and effect of rehabilitation based on the position information and the display control unit displays an evaluation result obtained by the evaluation unit on the display unit.

According to the configuration (11), progressions and effects of rehabilitation may be objectively evaluated in more detail.

(12) The rehabilitation assistance system of any one of (1) to (11) further includes a display device and the peg board is an image displayed on the display device.

According to the configuration (12), a universal display device may function as the peg board, thereby increasing a degree of freedom in selecting a site where rehabilitation is performed.

(13) The rehabilitation assistance system of (12) further includes a storage unit that stores images representing a plurality of types of peg boards, and the display is configured to selectively display one of the images representing the plurality of types of peg boards.

According to the configuration (13), a plurality of types of trainings may be provided to the subject using a single display device. For example, an optimal peg board according to a restoration state of the finger function of the subject may be displayed on the display device.

BRIEF DESCRIPTION OF DRAWINGS

FIG. 1A is a functional block diagram showing a rehabilitation assistance system according to one embodiment of the present invention.

FIGS. 8A and 8B are views showing displaying examples by the display device.

DETAILED DESCRIPTION OF EMBODIMENTS

Figure 1B:
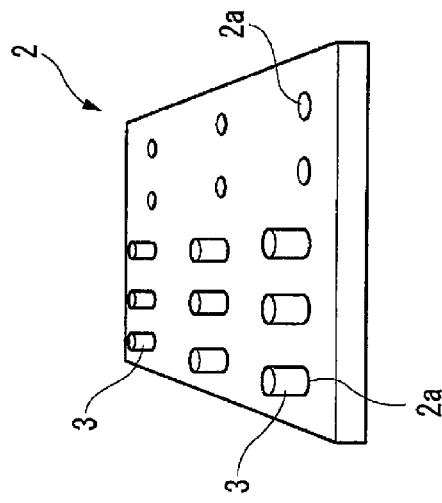
FIG. 1B is a schematic diagram showing a peg board 2 and pegs 3.

Examples of embodiments according to the present invention will be now described in detail with reference to the accompanying drawings. FIG. 1A is a functional block diagram showing a rehabilitation assistance system 1 (hereinafter, abbreviated to the assistance system 1) according to one embodiment of the present invention. FIG. 1B is a schematic diagram showing a peg board 2 and pegs 3.

The assistance system 1 has the peg board 2 and at least one peg 3. The peg board 2 is a plane or three-dimensional device having a plurality of holes 2a formed therein. A plurality of pegs 3 are inserted in any of the plurality of holes 2a. The plurality of pegs 3 includes several types. Types of pegs 3 are distinguished by shapes, sizes, colors or the like and may be properly used, such as by changing levels of difficulty in holding ability as a rehabilitation is progressed. Also, the plurality of holes 2a includes several types to correspond to types of pegs 3. Namely, types of holes 2a are distinguished by shapes, sizes, colors or the like. In FIG. 1B, several types of cylindrical pegs having different diameters are illustrated. For example, a subject pulls off a specified peg 3 from a hole 2a and then inserts the peg 3 into another specified hole 2a on the basis of an instruction of a medical personnel. In order to increase variations of works as the rehabilitation is progressed, a peg 3, which is placed at a location other than the holes 2a, may be inserted into a specified hole 2a.

The assistance system 1 has a position information acquisition unit 4. The position information acquisition unit 4 is configured to acquire position information indicating a position of a peg 3 relative to a predetermined position on the peg board 2. For example, the position information may be composed of three-dimensional coordinates in a space including the peg board 2. Alternatively, the position information may be composed of two-dimensional coordinates indicating only a position on the peg board 2.

The predetermined position is, for example, a position of a hole 2a at a specified moving destination for any one peg 3. In this case, by acquiring the position information, a distance between the hole 2a at the specified moving destination and the peg 3 may be grasped. Alternatively, a reference position on the peg board 2 may be designated as an origin point in the three-dimensional coordinate or the two-dimensional coordinate and then the origin point may be designated as the predetermined position. In this case, by acquiring the position information, a relative position of the peg 3 to the peg board 2 may be grasped.

By continuously acquiring position information of the peg 3, a moving path of the peg 3 relative to the predetermined position may be grasped. In other words, the moving path of the peg 3 is a moving path of fingers of the subject who grips the peg 3. Also, when position information of the peg 3 are acquired at constant time intervals, a moving speed of the peg 3 may be grasped.

According to this configuration, various information as well as whether or not the peg 3 is inserted into the hole 2a at the specified moving destination may be acquired. For example, when the subject cannot insert the peg 3 into the specified hole 2a, a conventional configuration may grasp only the fact that the subject does not insert the peg 3 into the hole 2a. However, according to the configuration as described above, how degree the subject can approach the peg 3 to the vicinity of the hole 2a may be grasped. In addition, which path the subject moves the peg 3, how high speed the subject moves the peg 3, how long time the subject spends moving the peg 3 and the like may be grasped. Accordingly, a degree of restoration of a finger function of the subject may be more accurately evaluated in objective and diversified manners.

Figure 2A:
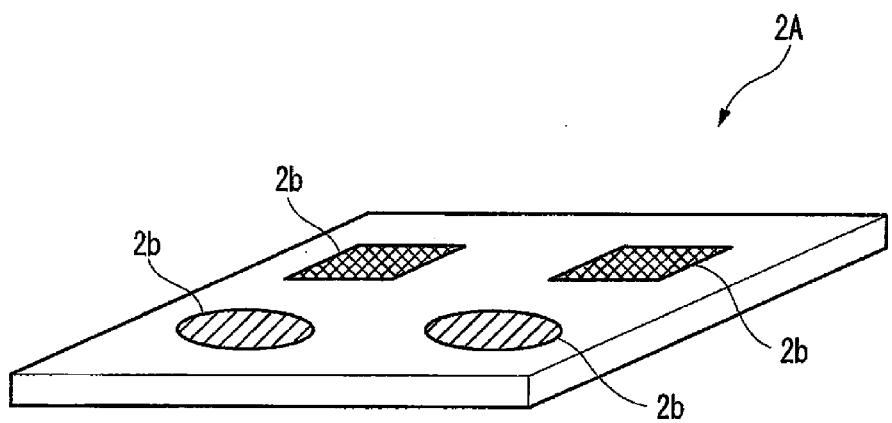
FIGS. 2A and 2B are views showing a variation of a peg board equipped in the system.

The peg board 2 does not need to have holes 2a formed therein. For example, a peg board 2A according to a variation shown in FIG. 2A has predetermined-shaped FIG. 2b drawn thereon. The FIG. 2b may be painted to be distinguished by a plurality of colors as needed. In this case, the subject moves a specified peg 3 so that a bottom surface thereof is overlapped with a specified FIG. 2b.

Figure 3A:
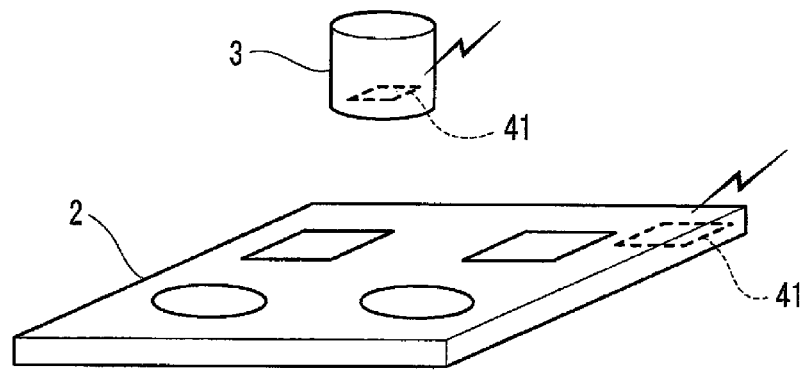
FIGS. 3A to 3C are views showing an example of a position information acquisition unit equipped in the system.

As shown by a broken line in FIG. 1A, the position information acquisition unit 4 may be configured to include a sensor 41. In this case, the position information acquisition unit 4 receives a signal outputted from the sensor 41 via wire or wireless communication and processes the signal to acquire the position information. A type of the sensor 41 may be properly determined if a positional relationship between the peg board 2 and the peg 3 may be grasped. For example, the sensor 41 includes at least one of an acceleration sensor, an angular velocity sensor, a magnetic sensor, an atmospheric pressure sensor and a motion sensor. Also, depending on types of the sensor 41, the number and arrangement thereof may be properly determined. As shown in FIG. 3A, the sensor 41 is provided on at least one of the peg board 2 and the peg 3.

According to this configuration, a suitable sensor may be selected depending on information desired to be grasped, so that the positional relationship between the peg board 2 and the peg 3 may be accurately grasped. Accordingly, a degree of restoration of the finger function of the subject may be accurately and objectively evaluated in more detail.

Figure 3B:
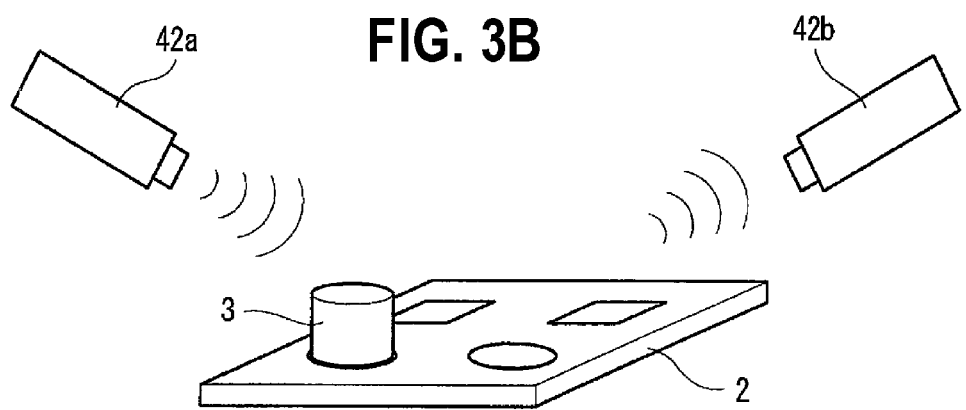

Alternatively or in addition to the configuration having the sensor 41, as shown by a broken line in FIG. 1A, the position information acquisition unit 4 may be configured to include a wave transmitting/receiving portion 42. As shown in FIG. 3B, the wave transmitting/receiving portion 42 includes a wave transmitting portion 42a and a wave receiving portion 42b. The wave transmitting portion 42a is configured to output a wave (such as infrared ray or ultrasonic wave) having a predetermined wavelength toward the peg board 2 and the peg 3. The wave receiving portion 42b is configured to detect the wave outputted from the wave transmitting portion 42a and then reflected by the peg board 2 and the peg 3. As used herein, the term 'wave' is intended to include both a transvers wave, such as electromagnetic wave, and a longitudinal wave, such as sound wave.

In this case, the position information acquisition unit 4 receives a signal outputted from the wave receiving portion 42b via wire or wireless communication and processes the signal to acquire the position information. A type of the wave transmitting/receiving portion 42 may be properly determined if the positional relationship between the peg board 2 and the peg 3 may be grasped. Also, depending on types of the wave transmitting/receiving portion 42, the number and arrangement of the wave transmitting portion 42a and the wave receiving portion 42b may be properly determined.

Figure 3C:
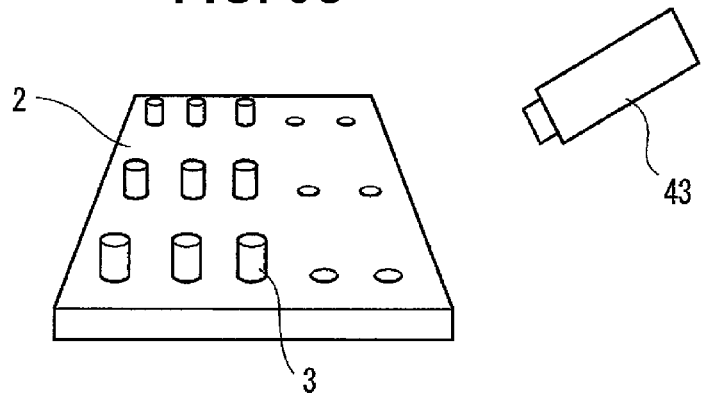

Alternatively or in addition to the configuration having at least one of the sensor 41 and the wave transmitting/receiving portion 42, as shown by a broken line in FIG. 1A, the position information acquisition unit 4 may be configured to include a imaging portion 43. As shown in FIG. 3C, the imaging portion 43 is configured to picture the peg board 2 and the peg 3 using a predetermined wave band (such as visible ray band or infrared ray band). In this case, the position information acquisition unit 4 processes an image obtained by the imaging portion 43 to acquire the position information. For example, the position information acquisition unit 4 identifies a shape or color of the peg 3 by image recognition technology to grasp a position of the peg 3 in a space including the peg board 2.

According to this configuration, the positional relationship between the peg board 2 and the peg 3 may be grasped without adding a mechanism, such as a sensor, to conventional peg board and pegs. Accordingly, a system, which may more accurately and objectively evaluate a degree of restoration of the finger function of the subject, may be provided at lower costs.

Figure 2B:
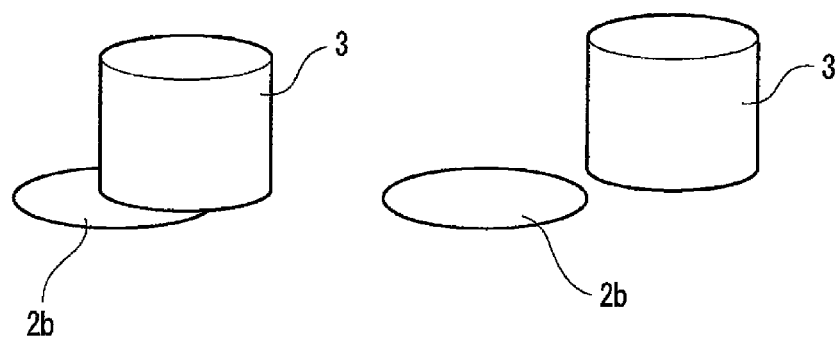

Further, in a case of a variation shown in FIG. 2, an area of the FIG. 2b covered with the bottom surface of the peg is recognized from an image so that a degree of achievement of an instruction may be evaluated.

According to this configuration, the positional relationship between the peg board 2 and the peg 3 may be grasped without adding a mechanism, such as a sensor, to conventional peg board and pegs. Accordingly, a system, which may more accurately and objectively evaluate a degree of restoration of the finger function of the subject, may be provided at lower costs.

When the position information is acquired by the image recognition technology, a marker, which is immovable regardless of movement of the subject and the peg 3, may be installed in a space included in an image obtained by the imaging portion 43, for the purpose of enhancing the accuracy of acquiring the position information. For example, when the marker is provided on or near the peg board 2, the position information may be acquired from a distance relative to the marker.

According to this configuration, it is possible to further enhance the accuracy of image recognition in a simple manner while limiting costs.

As shown in a broken line in FIG. 1A, the assistance system 1 may be configured to include a recoding unit 5. The recording unit 5 is configured to record the position information acquired by the position information acquisition unit 4 in association with acquisition date and time of the position information. Also, the recording portion 5 may be configured to record the position information in association with at least one of information for specifying the subject, information for specifying a situation, at which the position information is acquired, and an achievement target for rehabilitation. The recording unit 5 may be embodied by a mass storage device such as a hard disk drive, a portable media such as an optical disk, a memory card or a USB memory, an external storage device on a network or the like. The position information recorded in the recording unit 5 may be referred as needed.

In this configuration, the past training information and the current training information may be compared in terms of position information, speed and time as well as whether or not a peg 3 is inserted into a hole 2a at a specified moving destination. Accordingly, a degree of restoration of the finger function of the subject may be more accurately evaluated in objective and diversified manners.

As shown by a broken line in FIG. 1A, the assistance system 1 may be configured to include a display unit 5 and a display control unit 7. Examples of the display unit 6 may include a display screen of a stationary display device, a display screen of a mobile terminal such as a note PC or a tablet PC, or a head mount display mounted on a head of the subject or the like. The display control unit 7 is configured to display on the display unit 6 at least one of position information, which is acquired by the position information acquisition unit 4, and position information, which is stored in the recording unit 5. Additionally or alternatively, the display control unit 7 is configured to display on the display unit 6 an image based on at least one of position information, which is acquired by the position information acquisition unit 4, and position information, which is stored in the recording unit 5.

Figure 4:
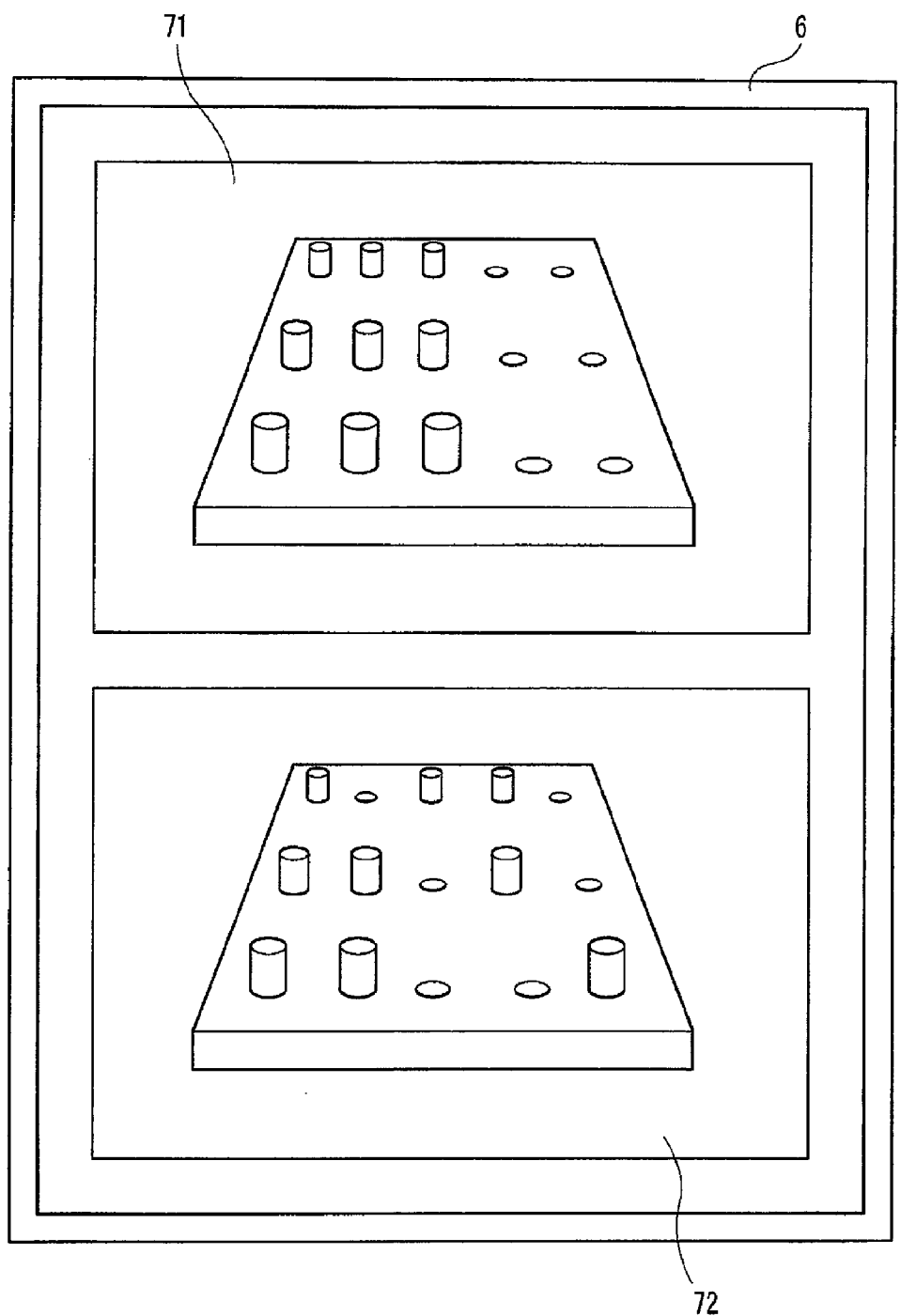
FIG. 4 is a view showing a displaying example by a display unit equipped in the system.

For example, when a plurality of rehabilitation are preformed, the display control unit 7 displays, on the display unit 6, position information or image, which is acquired during the current training, and position information or image, which is acquired during the past training and red from the recording unit 5. The image may include fingers of the subject as well as the peg 3. In an example shown in FIG. 4, the display unit 6 displays an image 71 pictured during the current training and an image 72 pictured during the last training.

According to this configuration, the current training image and the last training image may be viewed at the same time and compared. Therefore, the subject may also visually identify progressions and effects of rehabilitation. Accordingly, a degree of restoration of the finger function of the subject may be more accurately and objectively evaluated.

The position information or image displayed on the display unit 6 may not be position information or image which is acquired by the position information acquisition unit 4 in the past and then stored in the recording unit 5. As shown by a broken line in FIG. 1A, the assistance system 1 may be configured to include a first virtual image generation unit 8. The first virtual image generation unit 8 is configured to generate a virtual image based on the position information as an image to be displayed on the display unit 6. Examples of the virtual image may include a computer graphic image, which represents an exterior appearance of at least one of the peg board 2 and the peg 3, an image including lines or arrows for representing the moving path of the peg 3, or the like. As the position information, at least one of those acquired by the position information acquisition unit 4 and those stored in the recording unit 5 may be employed. For example, of the image 71 representing the current training result and the image 72 representing the last training result shown in FIG. 4, at least the image 72 representing the last training result may be a virtual image generated by the first virtual image generation unit 8.

Figure 5A:
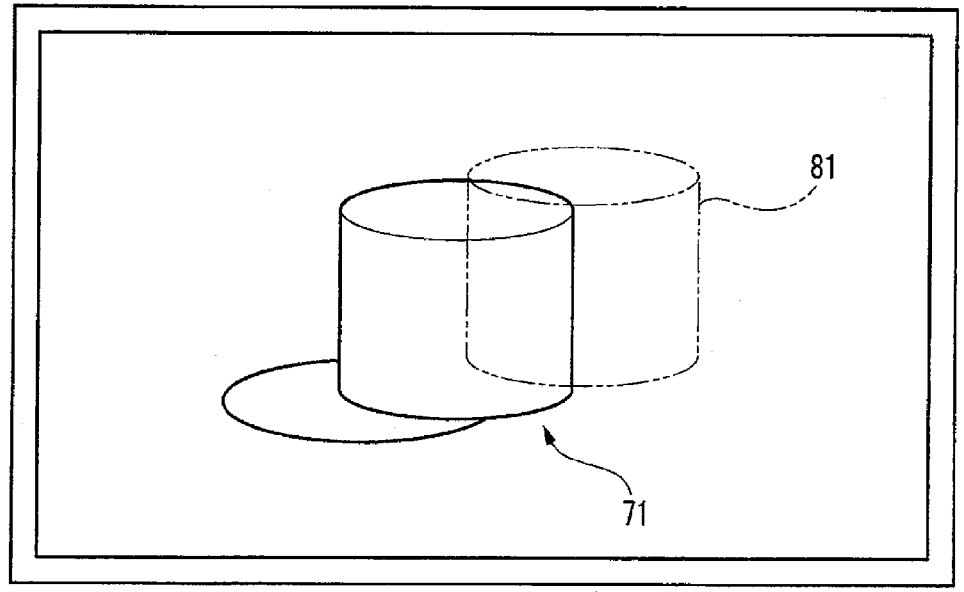
FIGS. 5A and 5B are views showing displaying examples by a display unit equipped in the system.
Figure 5B:
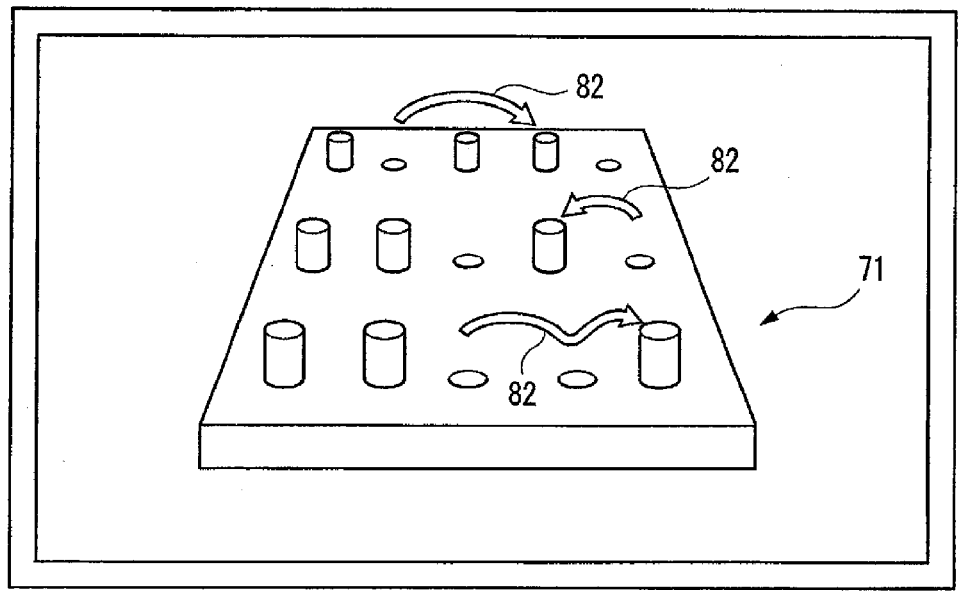

A configuration in which an image pictured by the imaging portion 43 is displayed to be overlapped with a virtual image may be contemplated. For example, in FIG. 5A, a virtual peg image 81 generated by the first virtual image generation unit 8 is displayed to be overlapped with the image 71 pictured by the imaging portion 43. The virtual peg image 81 represents an arrangement of a peg, for example, in the past training. Alternatively, as shown in FIG. 5B, virtual line images 82 representing the moving path of the peg are displayed to be overlapped with the image 71 pictured by the imaging portion 43.

Additionally or alternatively, as shown by a broken line in FIG. 1A, the assistance system 1 may be configured to include a second virtual image generation unit 9. The second virtual image generation unit 9 is configured to generate a virtual image based on information related to the achievement target for rehabilitation as an image to be displayed on the display unit 6. Examples of the virtual image may include a computer graphic image, which represents an exterior appearance of at least one of the peg board 2 and the peg 3, an image including lines or arrows for representing the moving path of the peg 3, or the like. Namely, for example, one of the image 71 and the image 72 shown in FIG. 4 may be an image representing an arrangement of pegs for indicating an achievement target for rehabilitation. Also, the virtual peg image 81 shown in FIG. 5A may represent an arrangement of a peg for indicating an achievement target for rehabilitation. In addition, at least one of the virtual line images 82 shown in FIG. 5B may represent a moving path of the peg for indicating an achievement target for rehabilitation.

According to the configuration as described above, results of training or progressions and effects of rehabilitation may be visually identified even in the case of a configuration in which the imaging portion is not included. Also, because the virtual image may be generated if position information is stored, a data size to be stored may be reduced compared with a case that image data is used. Accordingly, the costs of constructing a system in which a degree of restoration of the finger function of the subject may be accurately and objectively evaluated in more detail may be limited.

As shown by a broken line in FIG. 1A, the assistance system 1 may be configured to include an evaluation unit 10. The evaluation unit 10 is configured to evaluate at least one of progression and effect of rehabilitation based on position information. As the position information, at least one of those acquired by the position information acquisition unit 4 and those stored in the recording unit 5 may be employed. In this case, the display control unit 7 displays an evaluation result obtained by the evaluation unit 10 on the display unit 6. The evaluation result may be displayed on a separate display device, instead of or in addition to the display unit 6.

As information acquired by the position information acquisition unit 4, position coordinates of a peg may be acquired in time-series. Therefore, a moving path of the peg and a moving speed of the peg, a moving region of the peg, a maximum reaching point of the peg, an average height of the peg, a starting position and a final position of the peg, a moving time of the peg and the like may be acquired. Using such information, the evaluation unit 10 may more accurately and objectively evaluate a degree of restoration of the finger function of the subject.

For example, from the moving path of the peg, comparison to a moving path in the past or a moving path of an achievement target may be performed, or instability or smoothness thereof may be evaluated. Also, for example, from the moving speed of the peg, speed inhomogeneity, whether or not the peg may be moved at a constant speed or the like may be evaluated. Further, for example, from the moving region of the peg or the maximum reaching point of the peg, easiness in movement of a joint or the like may be evaluated. Further, for example, from the average height of the peg, whether or not the peg may be moved at a constant speed/height or the like may be evaluated. In addition, for example, from the starting position and the final position of the peg and the moving time of the peg, how many and where pegs may be moved within a predetermined period of time and also how long time is required in moving the predetermined number of pegs or the like may be evaluated.

For example, the evaluation unit 10 is configured to evaluate a rate of concordance of a plurality of images. For example, from the fact that the rate of concordance at an initial stage of training is lower, it may be evaluated that restoration of the subject is progressed. Also, from the fact that the rate of concordance at stages in which training has been progressed is higher, it may be evaluated that reproducibility of an instructed operation is high.

Figure 6:
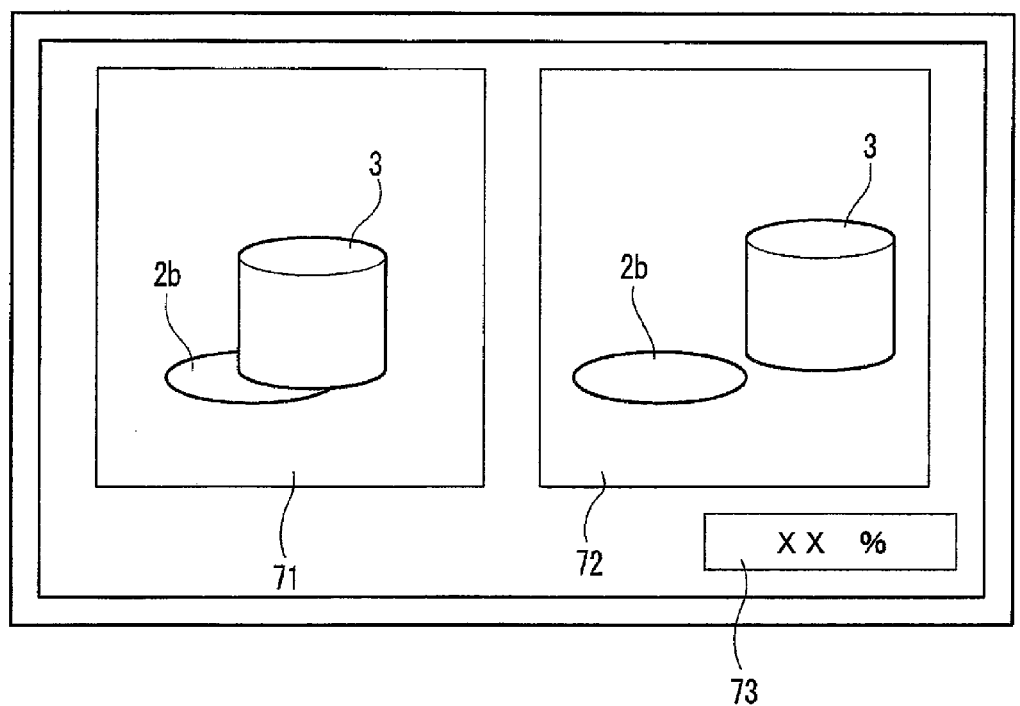
FIG. 6 is a view showing a displaying example by a display unit equipped in the system.

In this case, the display control unit 7 displays the evaluation result obtained by the evaluation unit 10 on the display unit 6. In an example shown in FIG. 6, in addition to the images 71 and 72 of the peg 3 at a plurality of time points, the display unit 6 displays, as the evaluation result 73, the rate of concordance corresponding to a difference between the two images. Alternatively, a degree of achievement of an instruction may be evaluated from how degree the bottom surface of the peg 3 is overlapped with the FIG. 2b. The evaluation result 73 may be displayed on another display device, instead of or in addition to the display unit 6.

According to this configuration, the result of rehabilitation may be more objectively evaluated. Accordingly, a degree of restoration of the finger function of the subject may be accurately and objectively evaluated in more detail.

Figure 7:
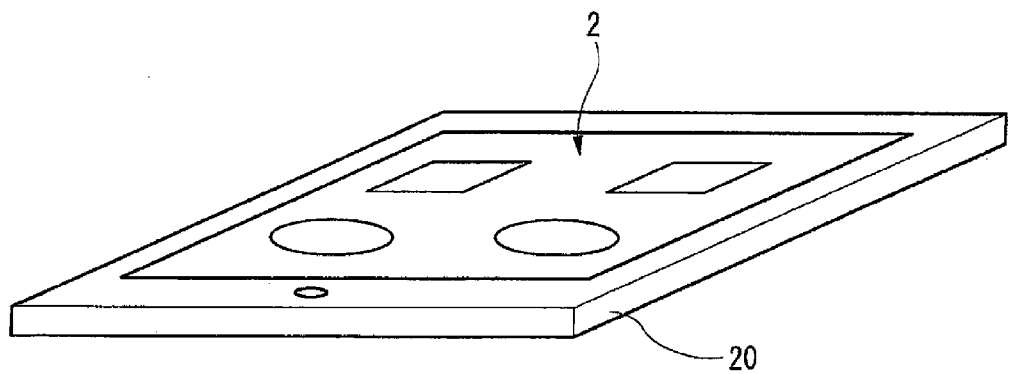
FIG. 7 is a view showing a display device equipped in the system.

As shown by a broken line in FIG. 1A, the assistance system 1 may be configured to include a display device 20. In this case, as shown in FIG. 7, the peg board 2 may be an image displayed on the display device 20 equipped in the assistance system 1. Examples of the display device 20 may include a display unit of a mobile terminal such as a tablet PC, an electronic paper or the like.

According to this configuration, a universal display device may function as the peg board, thereby increasing a degree of freedom in selecting a site where rehabilitation is performed. Accordingly, it is possible to more accurately and objectively evaluate a degree of restoration of the finger function of the subject, while reducing a burden on a training site.

As shown by a broken line in FIG. 1A, the assistance system 1 may be configured to include a storage 21. The storage unit 21 stores images representing a plurality of types of peg boards. As shown in FIGS. 8A and 8B, the display device 20 is configured to selectively display one of images representing the plurality of types of peg boards stored in the storage unit 21. The storage unit 21 may be equipped in the display device 20 and also may be a device connected to the display device 20 via communication network.

According to this configuration, a plurality of types of trainings may be provided to the subject using a single display device. For example, an optimal peg board according to a restoration state of the finger function of the subject may be displayed on the display device 20. Also, for a plurality of subjects, an optimal peg board according to a restoration state of the finger function of each of them may be displayed on the display device 20. It is possible to more accurately and objectively evaluate a degree of restoration of the finger function of the subject while reducing costs or an occupied space occurred in preparing a plurality of physical peg boards.

The foregoing embodiments are intended to facilitate understanding of the present invention, not to limit the invention. It is apparent that the invention may be changed and modified without departing from the spirit thereof and also the invention encompasses the equivalents.

(1) According to an aspect of the embodiment, a rehabilitation assistance system includes a peg board, a peg to be placed on the peg board by a subject, and a position information acquisition unit that acquires position information indicating a position of the peg relative to a predetermined position on the peg board.

According to the configuration (1), a degree of restoration of a finger function of the subject may be accurately and objectively evaluated in more detail.

(2) In the rehabilitation assistance system of (1), the position information acquisition unit includes a sensor provided on at least one of the peg and the peg board, and the position information acquisition unit acquires the position information based on an output from the sensor.

(3) In the rehabilitation assistance system of (2), the sensor includes at least one of an acceleration sensor, an angular velocity sensor, a magnetic sensor, an atmospheric pressure sensor and a motion sensor.

According to the configurations (2) and (3), a degree of restoration of the finger function of the subject may be accurately and objectively evaluated in more detail.

(4) In the rehabilitation assistance system of (1), the position information acquisition unit includes a wave transmitting portion that outputs a wave having a predetermined wavelength toward the peg board and the peg, and a wave receiving portion that detects the wave outputted from the wave transmitting portion and then reflected by the peg board and the peg, and the position information acquisition unit acquires the position information based on an output from the wave receiving portion.

According to the configuration (4), a system, which may more accurately and objectively evaluate a degree of restoration of the finger function of the subject in more detail, may be provided at lower costs.

(5) In the rehabilitation assistance system of (1), the position information acquisition unit includes a imaging portion for picturing the peg board and the peg, and the position information acquisition unit acquires the position information based on an image obtained by the imaging portion.

According to the configuration (5), a system, which may more accurately and objectively evaluate a degree of restoration of the finger function of the subject in more detail, may be provided at lower costs.

(6) In the rehabilitation assistance system of (5), the position information acquisition unit acquires the position information of the peg by extracting a feature point in the image obtained by the imaging portion.

According to the configuration (6), it is possible to more accurately and objectively evaluate a degree of restoration of the finger function of the subject while limiting costs.

(7) The rehabilitation assistance system of any one of (1) to (6) further includes a recording unit that records the position information in association with at least acquisition date and time of the position information.

According to the configuration (7), a degree of restoration of the finger function of the subject may be more accurately evaluated in objective and diversified manners.

(8) The rehabilitation assistance system of any one of (1) to (7) further includes a display unit that is visible by the subject, and a display control unit that displays on the display unit at least one of the position information and an image based on the position information.

According to the configuration (8), a degree of restoration of the finger function of the subject may be accurately and objectively evaluated in more detail.

(9) The rehabilitation assistance system of (8) further includes a first virtual image generation unit that generates a virtual image based on the position information as the image to be displayed on the display unit.

(10) The rehabilitation assistance system of (8) or (9) further includes a second virtual image generation unit that generates a virtual image based on information related to an achievement target for rehabilitation as the image to be displayed on the display unit.

According to the configurations (9) and (10), the costs of constructing a system, in which a degree of restoration of the finger function of the subject may be accurately and objectively evaluated in more detail, may be limited.

(11) The rehabilitation assistance system of any one of (8) to (10) further includes an evaluation unit that evaluates at least one of progression and effect of rehabilitation based on the position information and the display control unit displays an evaluation result obtained by the evaluation unit on the display unit.

According to the configuration (11), a degree of restoration of the finger function of the subject may be accurately and objectively evaluated in more detail.

(12) The rehabilitation assistance system of any one of (1) to (11) further includes a display device and the peg board is an image displayed on the display device.

According to the configuration (12), it is possible to more accurately and objectively evaluate a degree of restoration of the finger function of the subject, while reducing a burden on a training site.

(13) The rehabilitation assistance system of (12) further includes a storage unit that stores images representing a plurality of types of peg boards, and the display is configured to selectively display one of the images representing the plurality of types of peg boards.

According to the configuration (13), it is possible to more accurately and objectively evaluate a degree of restoration of the finger function of the subject while reducing costs or an occupied space occurred in preparing a plurality of physical peg boards.

What is claimed:

1. A rehabilitation assistance system comprising:
   a peg board;
   a peg to be placed on the peg board by a subject; and
   a position information acquisition unit that acquires position information indicating a position of the peg relative to a predetermined position on the peg board,
   wherein the position information acquisition unit includes: a wave transmitting portion that outputs a wave having a predetermined wavelength toward the peg board and the peg; and a wave receiving portion that detects the wave outputted from the wave transmitting portion and then reflected by the peg board and the peg, and
   wherein the position information acquisition unit acquires the position information based on an output from the wave receiving portion.

2. The rehabilitation assistance system according to claim 1, wherein the position information acquisition unit includes a sensor provided on at least one of the peg and the peg board, and wherein the position information acquisition unit acquires the position information based on an output from the sensor.

3. The rehabilitation assistance system according to claim 2, wherein the sensor includes at least one of an acceleration sensor, an angular velocity sensor, a magnetic sensor, an atmospheric pressure sensor and a motion sensor.

4. The rehabilitation assistance system according to claim 1, wherein the position information acquisition unit includes a imaging portion for picturing the peg board and the peg, and wherein the position information acquisition unit acquires the position information based on an image obtained by the imaging portion.

5. The rehabilitation assistance system according to claim 4, wherein the position information acquisition unit acquires the position information of the peg by extracting a feature point in the image obtained by the imaging portion.

6. The rehabilitation assistance system according to claim 1, further comprising a recording unit that records the position information in association with at least acquisition date and time of the position information.

7. The rehabilitation assistance system according to claim 1, further comprising: a display unit that is visible by the subject; and a display control unit that displays on the display unit at least one of the position information and an image based on the position information.

8. The rehabilitation assistance system according to claim 7, further comprising a first virtual image generation unit that generates a virtual image based on the position information as the image to be displayed on the display unit.

9. The rehabilitation assistance system according to claim 7, further comprising a second virtual image generation unit that generates a virtual image based on information related to an achievement target for rehabilitation as the image to be displayed on the display unit.

10. The rehabilitation assistance system according to claim 7, further comprising an evaluation unit that evaluates at least one of progression and effect of rehabilitation based on the position information, wherein the display control unit displays an evaluation result obtained by the evaluation unit on the display unit.

11. The rehabilitation assistance system according to claim 1, further comprising a display device, wherein the peg board is an image displayed on the display device.

12. The rehabilitation assistance system according to claim 11, further comprising a storage unit that stores images representing a plurality of types of peg boards, wherein the display is configured to selectively display one of the images representing the plurality of types of peg boards.

13. A rehabilitation assistance system comprising:
    a peg board;
    a peg to be placed on the peg board by a subject; and
    a position information acquisition unit that acquires position information indicating a position of the peg relative to a predetermined position on the peg board,
    wherein the position information acquisition unit includes a imaging portion for picturing the peg board and the peg, and
    wherein the position information acquisition unit acquires the position information based on an image obtained by the imaging portion.

14. A rehabilitation assistance system comprising:
    a peg board;
    a peg to be placed on the peg board by a subject;
    a position information acquisition unit that acquires position information indicating a position of the peg relative to a predetermined position on the peg board;
    a display unit that is visible by the subject;
    a display control unit that displays on the display unit at least one of the position information and an image based on the position information; and
    an evaluation unit that evaluates at least one of progression and effect of rehabilitation based on the position information,
    wherein the display control unit displays an evaluation result obtained by the evaluation unit on the display unit.

15. A rehabilitation assistance system comprising:
    a peg board;
    a peg to be placed on the peg board by a subject;
    a position information acquisition unit that acquires position information indicating a position of the peg relative to a predetermined position on the peg board;
    a display device; and
    a storage unit that stores images representing a plurality of types of peg boards,
    wherein the peg board is an image displayed on the display device, and
    wherein the display is configured to selectively display one of the images representing the plurality of types of peg boards.

* * * * *